(12) United States Patent
Rosenstingl et al.

(10) Patent No.: US 9,290,523 B2
(45) Date of Patent: Mar. 22, 2016

(54) PROCESS FOR PREPARING UREA-CONTAINING SILANES

(71) Applicant: Evonik Industries AG, Essen (DE)

(72) Inventors: Sebastian Rosenstingl, Rheinfelden (DE); Ralph Moser, Freiburg i. Br. (DE); Caren Röben, Köln (DE); Rosemarie Burger, Inzlingen (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/711,478

(22) Filed: May 13, 2015

(65) Prior Publication Data

US 2015/0329574 A1    Nov. 19, 2015

(30) Foreign Application Priority Data

May 15, 2014  (DE) .......................... 10 2014 209 215

(51) Int. Cl.
*C07F 7/18*  (2006.01)
*C07F 7/08*  (2006.01)

(52) U.S. Cl.
CPC ............. *C07F 7/1892* (2013.01); *C07F 7/0892* (2013.01); *C07F 7/0818* (2013.01)

(58) Field of Classification Search
CPC ..... C07F 7/0892; C07F 7/0818; C07F 7/1892
USPC .................................................. 556/422, 427
See application file for complete search history.

(56) References Cited

U.S. PATENT DOCUMENTS

| | | | |
|---|---|---|---|
| 2,509,483 A | 5/1950 | Crouch | |
| 3,637,789 A | 1/1972 | Legendre | |
| 3,946,059 A | 3/1976 | Janssen et al. | |
| 2003/0191270 A1* | 10/2003 | Musa | ............................. 528/30 |

FOREIGN PATENT DOCUMENTS

| | | |
|---|---|---|
| DE | 3424534 | 1/1986 |
| DE | 10351735 | 12/2004 |
| DE | 60018483 | 1/2006 |
| EP | 1156053 | 11/2001 |
| JP | 2002201312 | 7/2002 |
| JP | 2002201312 A * | 7/2002 |
| JP | 2002311574 | 10/2002 |
| JP | 2008279736 | 11/2008 |
| WO | 99/55754 | 11/1999 |
| WO | 2013/087698 | 6/2013 |

OTHER PUBLICATIONS

Besson et al., J. Mat. Chem. 2009, 19, 4746-4752.*
Besson et al., "Soft route for monodisperse gold nanoparticles confined within SH- functionalized walls of mesoporous silica," J. Mat. Chem., 2009, 19, pp. 4746-4752.
German Search report for Application No. 102014209215.9 dated Jul. 31, 2014 (6 pages).
German Search report for Application No. 102014209221.3 dated Jul. 31, 2014 (5 pages).
German Search Report for Application No. 102014209226.4 dated Aug. 5, 2014 (6 pages).
German Search Report for Application No. 102014209239.6 dated Oct. 8, 2014 (6 pages).
German Search Report for Application No. 102014209233.7 dated Oct. 13, 2014 (6 pages).
Harpp et al., "Organic Sulfur Chemistry. X. Selective Desulfurization of Disulfides. Scope and Mechanism," Organic Sulfur Chemistry, 1970, pp. 2437-2443.
Wang et al, "Fabrication of Single-Hole Glutathione-Responsive Degradable Hollow Silica Nanoparticles for Drug Delivery," Applied Materials and Interfaces, American Chemical Society, 2014, 6, pp. 12600-12608.
European Patent Office Search Report for Application No. 15165635.2 dated Sep. 17, 2015 (3 pages).

* cited by examiner

*Primary Examiner* — Elvis O Price
(74) *Attorney, Agent, or Firm* — Michael Best & Friedrich LLP

(57) ABSTRACT

The invention relates to a process for preparing urea-containing silanes of the general formula I

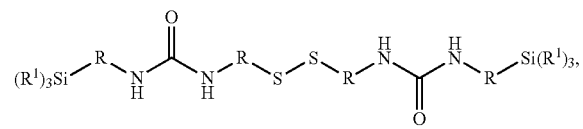

(I)

wherein
a diamine of the general formula II $$H_2N-R-S-S-R-NH_2 \quad (II)$$

is reacted with isocyanatosilane of the general formula III $$(R^1)_3Si-R-NCO \quad (III)$$

in water.

11 Claims, No Drawings

PROCESS FOR PREPARING UREA-CONTAINING SILANES

CROSS-REFERENCE TO RELATED APPLICATIONS

This patent application claims the benefit of priority to German Application No. 102014209215.9, filed on May 15, 2015, the disclosure of which is incorporated by reference herein in its entirety, and priority to which is hereby claimed.

The invention relates to a process for preparing urea-containing silanes.

CAS 1184961-62-3, 442527-46-0 and 498553-03-0 disclose compounds of the formula

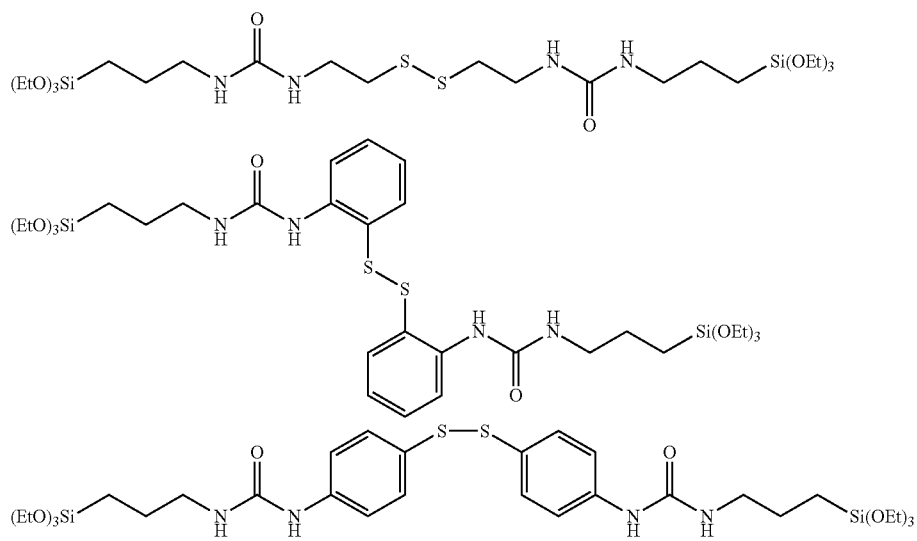

In addition, US 20030191270 A1 discloses silanes of the formula

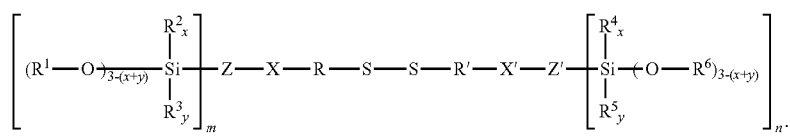

JP 2002201312 A discloses rubber modifiers of the formula

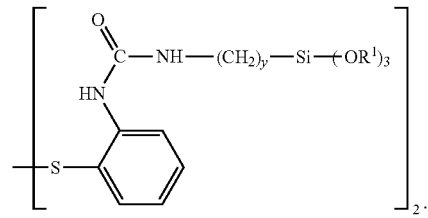

In addition, J. Mat. Chem. 2009, 19, 4746-4752 discloses gold nanoparticles within SH-functionalized framework structures formed from mesoporous silicas and the preparation of urea-containing silanes. In the known process, organic solvents are used.

A disadvantage of the known preparation process is that it is a complex process (neutralization in $H_2O$, extraction into $CH_2Cl_2$ phase, drying with $MgSO_4$, solvent removal, solvent exchange to THF, reaction in THF, solvent removal, precipitation/washing in pentane) having many process steps and organic solvent.

It is an object of the present invention to provide a process which, compared to the processes from the prior art, works without organic solvent and has fewer process steps.

The invention provides a process for preparing urea-containing silanes of the general formula I

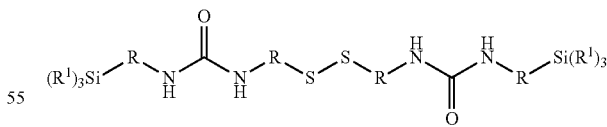

where $R^1$ are the same or different and are C1-C10 alkoxy groups, preferably methoxy or ethoxy group, C2-C10 cyclic dialkoxy group, phenoxy group, C4-C10 cycloalkoxy groups, C6-C20 aryl groups, preferably phenyl, C1-C10 alkyl group, preferably methyl or ethyl, C2-C20 alkenyl group, C7-C20 aralkyl group or halogen, preferably Cl, and R are the same or different and are a branched or unbranched, saturated or unsaturated, aliphatic, aromatic or mixed aliphatic/aromatic divalent C1-C30, preferably C1-C20, more preferably C1-C10, even more preferably C1-C7, especially preferably C2 and C3, hydrocarbon group optionally substituted by F—, Cl—, Br—, I—, —CN or HS—, which is characterized in that a diamine of the general formula II $$H_2N-R-S-S-R-NH_2 \quad (II)$$

is reacted with isocyanatosilane of the general formula III $$(R^1)_3Si-R-NCO \quad (III)$$

where R and $R^1$ are each as defined above, in water.

For the reaction, it is optionally possible to use an additional organic solvent.

The reaction can be conducted without organic solvent.

Urea-containing silanes may be mixtures of urea-containing silanes of the general formula I.

The process product may comprise oligomers which form through hydrolysis and condensation of the alkoxysilane functions of the urea-containing silanes of the general formula I.

R may preferably be

—$CH_2$—, —$CH_2CH_2$—, —$CH_2CH_2CH_2$—, —$CH_2CH_2CH_2CH_2$—, —$CH(CH_3)$—, —$CH_2CH(CH_3)$—,

—$CH(CH_3)CH_2$—, —$C(CH_3)_2$—, —$CH(C_2H_5)$—, —$CH_2CH_2CH(CH_3)$—, —$CH(CH_3)CH_2CH_2$—,

—$CH_2CH(CH_3)CH_2$—, —$CH_2CH_2CH_2CH_2CH_2$—, —$CH_2CH_2CH_2CH_2CH_2CH_2$—,

—$CH_2CH_2CH_2CH_2CH_2CH_2CH_2$—, —$CH_2CH_2CH_2CH_2CH_2CH_2CH_2CH_2$—,

—$CH_2CH_2CH_2CH_2CH_2CH_2CH_2CH_2CH_2$—,

—$CH_2CH_2CH_2CH_2CH_2CH_2CH_2CH_2CH_2CH_2$—, —$CH_2CH_2CH_2CH_2CH_2CH_2CH_2CH_2CH_2CH_2CH_2CH_2$—,

—$CH_2CH_2CH_2CH_2CH_2CH_2CH_2CH_2CH_2CH_2CH_2CH_2CH_2$—,

—$CH_2CH_2CH_2CH_2CH_2CH_2CH_2CH_2CH_2CH_2CH_2CH_2CH_2CH_2$—,

—$CH_2CH_2CH_2CH_2CH_2CH_2CH_2CH_2CH_2CH_2CH_2CH_2CH_2CH_2CH_2$—

—$CH_2$—$C_6H_4$—$CH_2CH_2$— or —$CH_2$—$CH_2$—$C_6H_4$—$CH_2$—.

Urea-containing silanes of the general formula I may preferably be:

$((EtO)_3Si-CH_2-NH-CO-NH-CH_2-S)_2$, $((EtO)_3Si-CH_2CH_2-NH-CO-NH-CH_2-S)_2$, $((EtO)_3Si-CH_2-NH-CO-NH-CH_2CH_2-S)_2$, $((EtO)_3Si-CH_2CH_2-NH-CO-NH-CH_2CH_2-S)_2$, $((EtO)_3Si-CH_2CH_2CH_2-NH-CO-NH-CH_2-S)_2$, $((EtO)_3Si-CH_2CH_2CH_2-NH-CO-NH-CH_2CH_2-S)_2$, $((EtO)_3Si-CH_2-NH-CO-NH-CH_2CH_2CH_2-S)_2$, $((EtO)_3Si-CH_2CH_2-NH-CO-NH-CH_2CH_2CH_2-S)_2$, $((EtO)_3Si-CH_2CH_2CH_2-NH-CO-NH-CH_2CH_2CH_2-S)_2$, $((MeO)_3Si-CH_2-NH-CO-NH-CH_2-S)_2$, $((MeO)_3Si-CH_2CH_2-NH-CO-NH-CH_2-S)_2$, $((MeO)_3Si-CH_2-NH-CO-NH-CH_2CH_2-S)_2$, $((MeO)_3Si-CH_2CH_2-NH-CO-NH-CH_2CH_2-S)_2$, $((MeO)_3Si-CH_2CH_2CH_2-NH-CO-NH-CH_2-S)_2$, $((MeO)_3Si-CH_2CH_2CH_2-NH-CO-NH-CH_2CH_2-S)_2$, $((MeO)_3Si-CH_2NH-CO-NH-CH_2CH_2CH_2-S)_2$, $((MeO)_3Si-CH_2CH_2-NH-CO-NH-CH_2CH_2CH_2-S)_2$ or $((MeO)_3Si-CH_2CH_2CH_2-NH-CO-NH-CH_2CH_2CH_2-S)_2$.

An especially preferred compound is of the formula $((EtO)_3Si-CH_2CH_2CH_2-NH-CO-NH-CH_2CH_2-S)_2$.

Diamines of the general formula II may preferably be:

$H_2N-CH_2-S-S-CH_2-NH_2$, $H_2N-CH_2CH_2S-S-CH_2-NH_2$.

$H_2N-CH_2CH_2S-S-CH_2CH_2NH_2$, $H_2N-CH_2-S-S-CH_2CH_2CH_2-NH_2$.

$H_2N-CH_2CH_2-S-S-CH_2CH_2CH_2-NH_2$ or $H_2N-CH_2CH_2CH_2-S-S-CH_2CH_2CH_2-NH_2$.

Isocyanatosilanes of the general formula III may preferably be:

$(C_2H_5O)_3Si-CH_2-NCO$, $(C_2H_5O)_3Si-CH_2CH_2-NCO$, $(C_2H_5O)_3Si-CH_2CH_2CH_2-NCO$, $(CH_3O)_3Si-CH_2-NCO$, (CH$_3$O)$_3$Si—CH$_2$CH$_2$—NCO or (CH$_3$O)$_3$Si—CH$_2$CH$_2$CH$_2$—NCO.

The urea-containing silane of the general formula I obtainable by the process according to the invention can be obtained in a yield of greater than 50%, preferably greater than 60%, more preferably greater than 70%, very preferably greater than 80%.

The soluble fraction in the product obtained by the process according to the invention in DMSO-d$^6$ or CDCl$_3$ is determined by adding an internal standard, for example triphenylphosphine oxide (TPPO), in DMSO-d6 or in CDCl$_3$, and a $^1$H NMR method known to those skilled in the art.

In relation to the diamines of the general formula II used, the amount of water may be more than 1% by weight, preferably more than 10% by weight, more preferably more than 50% by weight and most preferably more than 100% by weight.

The reaction can be conducted with exclusion of air.

The reaction may be carried out under an inert gas atmosphere, for example under argon or nitrogen, preferably under nitrogen.

The process of the invention can be carried out at atmospheric pressure, elevated pressure or reduced pressure. Preferably, the process according to the invention can be conducted at standard pressure.

Elevated pressure may be a pressure from 1.1 bar to 100 bar, preferably of 1.5 bar to 50 bar, more preferably of 2 bar to 20 bar and very preferably of 2 to 10 bar.

Reduced pressure may be a pressure of 1 mbar to 1000 mbar, preferably 1 mbar to 500 mbar, more preferably 1 mbar to 250 mbar, very preferably 5 mbar to 100 mbar.

The process according to the invention can be conducted between 0° C. and +100° C., preferably between 5° C. and 60° C., more preferably between 5° C. and 30° C.

For the process of the invention, diamines of the general formula II may be metered into isocyanatosilanes of the general formula III.

For the process of the invention, the isocyanatosilanes of the general formula III may preferably be metered into diamines of the general formula II.

The diamines of the general formula II, prior to the reaction with isocyanatosilanes of the general formula III, may be prepared from the hydrohalide salts of the diamines of the general formula IV $$\text{Hal}^-+\text{H}_3\text{N—R—S—S—R—NH}_3{}^+\text{Hal}^- \quad (IV)$$

by addition of a base, preferably NaOH or KOH, where Hal is F, Cl, Br or I, preferably Cl. The base can be added until a pH between 7 and 14 is established.

In the process according to the invention, the diamines of the general formula II can be used relative to isocyanatosilanes of the general formula III in a molar ratio of 1:1.70 to 1:2.20, preferably 1:1.75 to 1:2.10, more preferably in a ratio of 1:1.80 to 1:2.00.

The product prepared by the process according to the invention may have a residual content of diamines of the general formula II of less than 25 mol %, preferably less than 10 mol %, more preferably less than 5 mol %, very preferably less than 3 mol %.

The relative molar percentages of the diamines of the general formula II in the product prepared by the process according to the invention are determined in the $^{13}$C NMR by integration of the carbon atoms in the —$\underline{C}$H$_2$—NH$_2$ group of the diamines of the general formula II against the carbon atoms in the Si—$\underline{C}$H$_2$— group of the urea-containing silanes of the general formula I.

For the substance of the formula II H$_2$N—CH$_2$—CH$_2$—S—S—CH$_2$—CH$_2$—NH$_2$, for example, the integral of the carbon atoms of the —$\underline{C}$H$_2$—NH$_2$ group is used for the determination of the relative contents.

The product prepared by the process according to the invention may have a residual content of isocyanatosilanes of the general formula III of less than 10 mol %, preferably less than 5 mol %, more preferably less than 1 mol %, very preferably less than 0.1 mol %.

The relative molar percentages of the isocyanatosilanes of the general formula III in the product within a range of >1 mol %, prepared by the process according to the invention, are determined in the $^{13}$C NMR by integration of the carbon atoms in the —NCO group of the isocyanatosilanes of the general formula III against the carbon atoms in the Si—$\underline{C}$H$_2$— group of the urea-containing silanes of the general formula I.

For the substance of the formula III (EtO)$_3$Si—CH$_2$—CH$_2$—CH$_2$—NCO, for example, the integral of the carbon atoms of the —N$\underline{C}$O group (δ=122.22 ppm) is used for the determination of the relative contents within a range of >1 mol %.

The relative molar percentages of the isocyanatosilanes of the general formula III in the product within a range of <1 mol %, prepared by the process according to the invention, are determined by quantitative FT-IR spectroscopy known to those skilled in the art. The method is calibrated by using calibration solutions of suitable concentration (for example in C$_2$Cl$_4$). For the measurement, about 1 g sample is weighed into a 25 ml rollneck bottle, and 25 g of C$_2$Cl$_4$ are added. The sample is agitated on an agitator for 1-2 hours. Thereafter, the lower liquid phase is metered cautiously into a 20 mm IR cuvette and analysed by FT-IR spectroscopy (4000-1200 cm-1, resolution 2 cm$^{-1}$). Under the same conditions, a spectrum of the solvent is recorded for subtraction.

For the substance of the formula III (EtO)$_3$Si—CH$_2$—CH$_2$—CH$_2$—NCO, for example, the wavelength of the valence vibration of the —NCO group at 2270 cm$^{-1}$ is used for the determination of the relative contents within a range of <1 mol %.

The product prepared by the process according to the invention may have a residual content of hydrohalide salt of the diamines of the general formula IV of less than 25 mol %, preferably less than 10 mol %, more preferably less than 5 mol %, very preferably less than 3 mol %.

The relative molar percentages of the hydrohalide salts of the diamines of the general formula IV in the product prepared by the process according to the invention are determined in the $^{13}$C NMR by integration of the carbon atoms in the —$\underline{C}$H$_2$—NH$_2$.HCl group of the hydrohalide salts of the diamines of the general formula IV against the carbon atoms in the Si—$\underline{C}$H$_2$— group of the urea-containing silanes of the general formula I.

For the substance of the formula IV HCl.H$_2$N—CH$_2$—CH$_2$—S—S—CH$_2$—CH$_2$—NH$_2$.HCl, for example, the integral of the carbon atoms of the S—CH$_2$—$\underline{C}$H$_2$—NH$_2$.HCl group (δ=37.82 ppm) or of the S—$\underline{C}$H$_2$—CH$_2$—NH$_2$.HCl group (δ=33.79 ppm) is used for the determination of the relative contents.

The reaction product can subsequently be filtered and washed with water and/or an organic solvent, preferably alkane, more preferably pentane, hexane or heptane. It is preferable to wash with water and then with an alkane, more preferably hexane.

The product can be dried after filtration. The drying can be effected at temperatures of 20° C.-100° C., preferably of 25° C.-50° C. The drying can be effected at a reduced pressure of 1-500 mbar.

In a preferred embodiment, the process for preparing urea-containing silanes of the general formula I

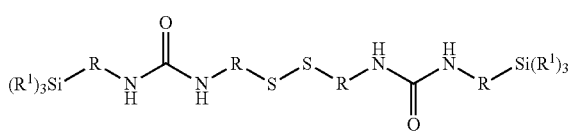

where R and $R^1$ are each as defined above may be characterized in that the hydrohalide salt of the diamine of the general formula IV

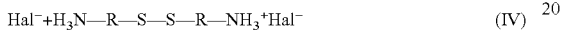

is dissolved in water and reacted with a base,
then the isocyanatosilane of the general formula III

is added, and the precipitated product is filtered off, washed with water and hexane, and dried.

The urea-containing silanes of the general formula I can be used as adhesion promoters between inorganic materials, for example glass beads, glass shards, glass surfaces, glass fibres, or oxidic fillers, preferably silicas such as precipitated silicas and fumed silicas, and organic polymers, for example thermosets, thermoplastics or elastomers, or as crosslinking agents and surface modifiers for oxidic surfaces.

The urea-containing silanes of the general formula I may be used as coupling reagents in filled rubber mixtures, examples being tyre treads, industrial rubber articles or footwear soles.

The advantage of the process according to the invention is that the preparation of urea-containing silanes of the general formula I is possible in one synthesis step without organic solvent.

A further advantage of the process according to the invention is that the reaction is effected within a relatively short period.

A further advantage of the process according to the invention is that a complex purification of the products obtained can be dispensed with.

EXAMPLES

Example 1

Preparation of $[(EtO)_3Si-(CH_2)_3-NH-C(=O)-NH-(CH_2)_2-S-]_2$ in Water (with Hexane Wash)

An N2-purged 2 l jacketed four-neck flask with precision glass stirrer, reflux condenser, internal thermometer and dropping funnel is initially charged with cystamine dihydrochloride (108.39 g, 0.47 mol, 1.00 eq) which was dissolved in demineralized water (940 ml). By means of a dropping funnel, 50% KOH solution (92.31 g, 0.82 mol, 1.75 eq) is metered in at 17-20° C. and the mixture is stirred for 15 min. Then 3-isocyanatopropyltriethoxysilane (221.05 g, 0.85 mol, 1.8 eq) is metered in at such a rate that an internal temperature of 30° C. is not exceeded. Thereafter, the mixture is stirred at 23° C. for one hour. The white suspension is filtered under pressure, rinsed with 200 ml of demineralized water and dried with dry $N_2$ for 2 h. The filtercake is washed with three portions of hexane (each of 150 ml) and dried again with dry $N_2$ for 1 h. The $[(EtO)_3Si-(CH_2)_3-NH-C(=O)-NH-(CH_2)_2-S-]_2$ product is a fine white powder (254.78 g, 92.8% of theory);

$^1$H NMR ($\delta_{ppm}$, 500 MHz, CDCl$_3$): 0.64 (4H, t), 1.22 (18H, t), 1.61 (4H, m), 2.78 (4H, m), 3.15 (4H, m), 3.52 (4H, m), 3.81 (12H, q), 5.2-6.5 (4H, br);

$^{13}$C NMR ($\delta_{ppm}$, 125 MHz, CDCl$_3$): 7.7 (2C), 18.3 (6C), 23.8 (2C), 38.8 (2C), 38.9 (2C), 42.8 (2C), 58.3 (6C), 159.0 (2C).

$^{29}$Si NMR ($\delta_{ppm}$, 100 MHz, CDCl$_3$): −45.7 (97.4% silane), −53.5 (2.6% M structures);

Soluble fractions in CDCl$_3$ using TPPO internal standard: 94.4%;

Water content (DIN 51777): 0.4%;
Initial melting point: 106-110° C.;
Residual isocyanate content: 0.04%

Example 2

Preparation of $[(EtO)_3Si-(CH_2)_3-NH-C(=O)-NH-(CH_2)_2-S-]_2$ in Water (without Hexane Wash)

An N2-purged 1 l jacketed four-neck flask with precision glass stirrer, reflux condenser, internal thermometer and dropping funnel is initially charged with cystamine dihydrochloride (108.39 g, 0.47 mol, 1.00 eq) which was dissolved in demineralized water (382 ml). By means of a dropping funnel, 50% KOH solution (92.31 g, 0.82 mol, 1.75 eq) is metered in at 15-23° C. and the mixture is stirred for 30 min. Then 3-isocyanatopropyltriethoxysilane (221.05 g, 0.85 mol, 1.8 eq) is metered in at such a rate that an internal temperature of 30° C. is not exceeded. Thereafter, the mixture is stirred at 24° C. for one hour. The white suspension is filtered under pressure, rinsed with three portions of demineralized water (340 ml in total) and dried with dry $N_2$ for 2 h. The filtercake is dried in an $N_2$ stream in a rotary evaporator at 35° C. and 166 mbar for 7 h, at 35° C. and 150 mbar for 10 h and at 35° C. and 100 mbar for 9 h. The $[(EtO)_3Si-(CH_2)_3-NH-C(=O)-NH-(CH_2)_2-S-]_2$ product is a fine white powder (246.38 g, 90.7% of theory);

$^1$H NMR ($\delta_{ppm}$, 500 MHz, DMSO-d6): 0.52 (4H, t), 1.14 (18H, t), 1.42 (4H, m), 2.74 (4H, m), 2.96 (4H, m), 3.29 (4H, m), 3.74 (12H, q), 6.05 (4H, m);

$^{13}$C NMR ($\delta_{ppm}$, 125 MHz, DMSO-d6): 7.3 (2C), 18.2 (6C), 23.5 (2C), 38.5 (2C), 39.6 (2C), 42.0 (2C), 57.7 (6C) 157.9 (2C).

$^{29}$Si NMR ($\delta_{ppm}$, 100 MHz, DMSO-d6): −45.3 (100% silane);

Soluble fractions in d6-DMSO using TPPO internal standard: 86.0%;

Water content (DIN 51777): 0.7%;
Initial melting point: 97° C.;
Residual isocyanate content: 0.08%

Example 3

Comparative Example

Preparation of $[(EtO)_3Si-(CH_2)_3-NH-C(=O)-NH-(CH_2)_2-S-]_2$ in Organic Dichloromethane and THF Solvents A dry, N2-purged three-neck flask with stirrer, reflux condenser, internal thermometer and dropping funnel is initially charged with cystamine dihydrochloride (22.52 g, 0.10 mol, 1.00 eq) which is dissolved in dichloromethane (100 ml). By means of a dropping funnel, 50% KOH solution (11.5 ml, 0.20 mol, 2.00 eq) is metered in. The resultant suspension is brought into solution with 50 ml of demineralized water, 6.5 ml of 50% KOH solution are additionally added, and the mixture is stirred for 2 h. The two phases are separated and the aqueous phase is extracted with dichloromethane (3×50 ml). The combined organic phases are dried over MgSO$_4$, filtered and freed of the solvent on a rotary evaporator. The resultant pale yellow, viscous oil (cystamine, 12.07 g) was taken up in THF (100 ml), a dropping funnel is used to meter in 3-isocyanatopropyltriethoxysilane (49.47 g, 0.20 mol, 2.00 eq) and the mixture is stirred at 23° C. overnight. After the reaction has ended, the solvent is removed on a rotary evaporator. The resultant white solid is taken up in fresh THF (84 ml) and precipitated with addition of n-pentane (521 ml) at 8° C. The suspension is filtered under pressure, and the filtercake is washed with n-pentane (3×100 ml) and dried with dry N$_2$. The [(EtO)$_3$Si—(CH$_2$)$_3$—NH—C(=O)—NH—(CH$_2$)$_2$—S—]$_2$ product is a fine white powder (50.42 g, 77.9% of theory);

$^{29}$Si NMR ($\delta_{ppm}$, 100 MHz, DMSO-d6): −40.5 (91.2% silane), −48.2 (8.9% M structures).

What is claimed is:

1. A process for preparing a urea-containing silane of formula I

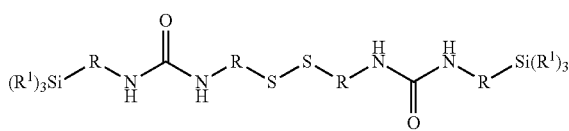

(I)

where each R$^1$ is independently selected from the group consisting of a C1-C10 alkoxy group, a C2-C10 cyclic dialkoxy group, a phenoxy group, a C4-C10 cycloalkoxy group, a C6-C20 aryl group, a C1-C10 alkyl group, a C2-C20 alkenyl group, a C7-C20 aralkyl group or a halogen, and each R is independently a branched or unbranched, saturated or unsaturated, aliphatic, aromatic or mixed aliphatic/aromatic divalent C1-C30 hydrocarbon group, the process comprising reacting a diamine of formula II

H$_2$N—R—S—S—R—NH$_2$ (II)

with an isocyanatosilane of formula III (R$^1$)$_3$Si—R—NCO (III)

in water.

2. The process of claim 1, wherein the urea-containing silane is ((EtO)$_3$Si—CH$_2$—NH—CO—NH—CH$_2$—S)$_2$, ((EtO)$_3$Si—CH$_2$CH$_2$—NH—CO—NH—CH$_2$—S)$_2$, ((EtO)$_3$Si—CH$_2$—NH—CO—NH—CH$_2$CH$_2$—S)$_2$, ((EtO)$_3$Si—CH$_2$CH$_2$—NH—CO—NH—CH$_2$CH$_2$—S)$_2$, ((EtO)$_3$Si—CH$_2$CH$_2$CH$_2$—NH—CO—NH—CH$_2$—S)$_2$, ((EtO)$_3$Si—CH$_2$CH$_2$CH$_2$—NH—CO—NH—CH$_2$CH$_2$—S)$_2$, ((EtO)$_3$Si—CH$_2$—NH—CO—NH—CH$_2$CH$_2$CH$_2$—S)$_2$, ((EtO)$_3$Si—CH$_2$CH$_2$—NH—CO—NH—CH$_2$CH$_2$CH$_2$—S)$_2$ or ((EtO)$_3$Si—CH$_2$CH$_2$CH$_2$—NH—CO—NH—CH$_2$CH$_2$CH$_2$—S)$_2$.

3. The process of claim 1, wherein the reaction is conducted without organic solvent.

4. The process of claim 1, wherein the amount of water in the reaction is greater than 1% by weight, based on the diamines of the general formula II used.

5. The process of claim 1, wherein the temperature of the reaction is between 0° C. and +100° C.

6. The process of claim 1, wherein the diamines of the formula II, prior to reaction with the isocyanatosilanes of formula III, are prepared by adding a base to a hydrohalide salt of a diamine of formula IV Hal$^-$+H$_3$N—R—S—S—R—NH$_3$$^+$Hal$^-$ (IV).

7. The process of claim 6, wherein the base is NaOH or KOH.

8. The process of claim 6, wherein the base is added until a pH between 7 and 14 is established.

9. The process of claim 1, wherein the diamines of formula II are used relative to isocyanatosilanes of formula III in a molar ratio of 1:1.80 to 1:2.25.

10. The process of claim 1, wherein a reaction product is subsequently filtered off and washed with water and/or organic solvent.

11. The process of claim 10, wherein the product is further dried.

* * * * *